(12) United States Patent
Broell et al.

(10) Patent No.: US 8,791,296 B2
(45) Date of Patent: Jul. 29, 2014

(54) PROCESS FOR PREPARING METHACRYLIC ACID

(75) Inventors: Dirk Broell, Langen (DE); Hermann Siegert, Seeheim-Jugenheim (DE); Horst Hiltner, Muenster (DE); Thomas Krauss, Bickenbach (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 14/113,228

(22) PCT Filed: Apr. 24, 2012

(86) PCT No.: PCT/EP2012/057421
§ 371 (c)(1),
(2), (4) Date: Oct. 22, 2013

(87) PCT Pub. No.: WO2012/163600
PCT Pub. Date: Dec. 6, 2012

(65) Prior Publication Data
US 2014/0051886 A1    Feb. 20, 2014

(30) Foreign Application Priority Data
May 27, 2011   (DE) .......................... 10 2011 076 642

(51) Int. Cl.
*C07C 51/44* (2006.01)
(52) U.S. Cl.
USPC ....................................................... 562/600

(58) Field of Classification Search
CPC ........ C07C 51/04; C07C 51/09; C07C 51/44; C07C 253/08; C07C 231/06; C07C 67/20
See application file for complete search history.

(56) References Cited

U.S. PATENT DOCUMENTS

| | | | | |
|---|---|---|---|---|
| 3,882,167 A | * | 5/1975 | Lohmar et al. ................. | 560/205 |
| 5,393,918 A | * | 2/1995 | Dobson ......................... | 560/215 |
| 7,253,307 B1 | | 8/2007 | Carlson et al. | |
| 2003/0208093 A1 | | 11/2003 | Carlson et al. | |
| 2008/0091044 A1 | | 4/2008 | Yokota et al. | |

FOREIGN PATENT DOCUMENTS

EP    1 813 586    8/2007

OTHER PUBLICATIONS

Solomons, Organic Chemistry, 5th edition, 1992, John Wiley & Sons, Inc., New York, pp. 778-780.*
Osborn et al, Canadian Journal of Chemistry, Pressure Effect and Mechanism in Acid Catalysis VII. Hydrolysis of Methyl, Ethyl and t-Butyl Acetates, 1961, 30, pp. 1094-1100.*
International Search Report Issued Jul. 20, 2012 in PCT/EP12/57421 Filed Apr. 24, 2012.

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

The present invention relates to a process for preparing methacrylic acid based on the hydrolysis of methacrylic esters.

16 Claims, 1 Drawing Sheet

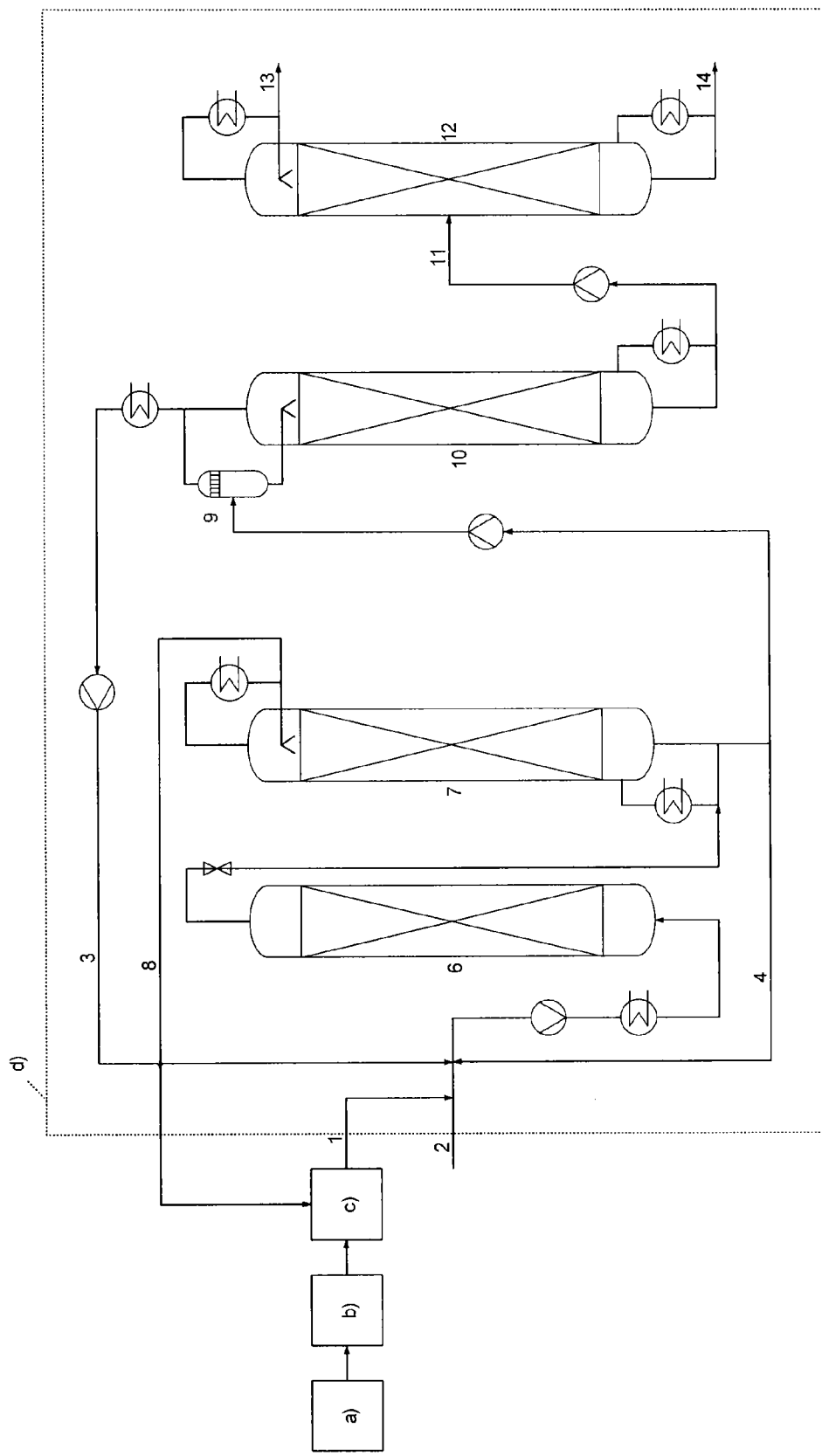

PROCESS FOR PREPARING METHACRYLIC ACID

CROSS-REFERENCE TO RELATED APPLICATIONS

This application is a National Stage of PCT/EP2012/057421 filed on Apr. 24, 2012. This application is based on and claims the benefit of priority to German Application No. 10 2011 076 642.1 filed on May 27, 2011.

BACKGROUND OF THE INVENTION

The present invention relates to a process for preparing methacrylic acid based on the hydrolysis of methacrylic esters.

The prior art discloses a multitude of processes for preparing methacrylic acid.

A customary procedure consists in the controlled oxidation of hydrocarbon gases, for example propylene or butylene. A disadvantage of these processes is the yields obtained thereby, which are relatively low when viewed overall.

In addition, methacrylic acid can be obtained by the reaction of methacrylamide with water. This process is described more particularly in U.S. Pat. No. 7,253,307. According to this publication, the reaction of methacrylamide with water can be effected in a stirred tank reactor or a tubular reactor. The reaction is preferably performed at a pressure of 3.65 to 7.70 bar and a temperature in the range from 50 to 210° C.

The processes described in U.S. Pat. No. 7,253,307 for preparation of methacrylic acid already lead to good yields with a high purity. However, methacrylic acid is an important product in the chemical industry, which serves as a starting material for many important products. Therefore, a maximum yield and a particularly high purity with low production costs are essential for the economic success of such a preparation process. Even relatively small improvements with regard to the yields, the service lives of the plants or similar process features lead to a significant advance with regard to the amounts of waste and the preparation costs.

α-Hydroxyisobutyric acid can likewise serve as a starting material for preparation of methacrylic acid. Such a process is described, for example, in U.S. Pat. No. 3,487,101, where the preparation of various methacrylic acid derivatives, especially methacrylic acid and methacrylic esters, proceeding from 2-hydroxyisobutyric acid (HIBA) in the liquid phase, is characterized in that the conversion of HIBA to methacrylic acid is performed in the presence of a dissolved basic catalyst at high temperatures between 180-320° C. in the presence of high-boiling esters (e.g. dimethyl phthalate) and internal anhydrides (e.g. phthalic anhydride). According to the patent, at HIBA conversions of >90% MA selectivities around 98% are achieved. No information is given as to the long-term stability of the liquid catalyst solution, more particularly the exhaustion of the anhydride used.

DE-A 1 191 367 relates to the preparation of methacrylic acid (MA) proceeding from HIBA in the liquid phase, characterized in that the conversion of HIBA to methacrylic acid is performed in the presence of polymerization inhibitors (for example copper powder) and in the presence of a catalyst mixture consisting of metal halides and alkali metal halides at high temperatures between 180-220° C. According to the patent, at HIBA conversions of >90%, MA selectivities of >99% are achieved. The best results are achieved with catalyst mixtures of zinc bromide and lithium bromide. It is common knowledge that the use of halide-containing catalysts at high temperatures places severe demands on the materials to be used, and these problems with regard to the entrained halogenated by-products present in the distillate also occur in downstream plant parts.

EP 0 487 853 describes the preparation of methacrylic acid proceeding from acetone cyanohydrin (ACH), characterized in that, in the first step, ACH is reacted with water at moderate temperatures in the presence of a heterogeneous hydrolysis catalyst and, in the second step, α-hydroxyisobutyramide is reacted with methyl formate or methanol/carbon monoxide to form formamide and methyl hydroxyisobutyrate (MHIB), and in the third step MHIB is hydrolysed in the presence of a heterogeneous ion exchanger with water to give HIBA, and, in the fourth step, HIBA is dehydrated, by allowing it to react in the liquid phase at high temperatures in the presence of a soluble alkali metal salt. Methacrylic acid preparation from HIBA is described at high conversions around 99% with more or less quantitative selectivities. The multitude of reaction steps necessary and the necessity of intermediate isolation of individual intermediates, more particularly also the performance of individual process steps at elevated pressure, make the process complicated and hence ultimately uneconomic. In addition, formamide is inevitably obtained, this compound in many cases being viewed as an unwanted by-product which has to be disposed of expensively.

DE-A 1 768 253 describes a process for preparing methacrylic acid by dehydration of HIBA, characterized in that HIBA is converted in the liquid phase at a temperature of at least 160° C. in the presence of a dehydration catalyst which consists of a metal salt of HIBA. Particularly suitable in this case are the alkali metal and alkaline earth metal salts of HIBA, which are prepared in situ in an HIBA melt by conversion of suitable metal salts. According to the patent, MA yields up to 95% from HIBA are described, the feed to the continuous procedure consisting from HIBA and approx. 1.5% by weight of HIBA alkali metal salt.

RU 89631 relates to a process for preparing methacrylic acid proceeding from HIBA by elimination of water in the liquid phase, characterized in that the reaction is performed in the absence of a catalyst with an aqueous solution of HIBA (up to 62% by weight of HIBA in water) under pressure at high temperatures of 200° C.-240° C.

There have additionally been detailed studies of the use of propene as a base raw material, obtaining methacrylic acid in moderate yields via the stages of hydrocarbonylation to isobutyric acid and dehydrogenating oxidation.

It is known that propanal or propionic acid, which are obtainable in industrial processes proceeding from ethylene and C-1 units such as carbon monoxide, can be used as a base raw material. In these processes, in an aldolizing reaction with formaldehyde, the β-hydroxycarbonyl compound formed in situ is dehydrated to the corresponding α,β-unsaturated compound. An overview of the standard processes for preparing methacrylic acid and the esters thereof can be found in the literature, for example Weissermel, Arpe "Industrielle organische Chemie" ["Industrial Organic Chemistry"], VCH, Weinheim 1994, 4th edition, p. 305 ff. or Kirk Othmer "Encyclopaedia of Chemical Technology", 3rd edition, Vol. 15, page 357.

It is therefore an object of the invention to provide a novel process for preparing methacrylic acid, which does not have the disadvantages mentioned, more particularly produces smaller amounts of waste acid, has a lower energy consumption, and enables higher yields and a lower water content in the end product.

BRIEF SUMMARY OF THE INVENTION

The object is achieved by a process for preparing methacrylic acid, comprising the following steps:

a) provision of acetone cyanohydrin
b) conversion of acetone cyanohydrin to methacrylamide
c) esterification of methacrylamide in the presence of alkanols to give the corresponding methacrylic ester
d) hydrolysis of the methacrylic ester to give methacrylic acid.

It has been found that, surprisingly, it is possible by the process according to the invention to provide a methacrylic acid synthesis implementable in a simple manner on the industrial scale. The process features the abovementioned advantages and a small by-product spectrum. The methacrylic acid obtained has purities of ≥99.5%.

It has been found that the use of heterogeneous catalysts in the hydrolysis step d) eliminates a separation stage for removal of the catalyst, and makes it possible to dispense with the use of sulphuric acid, which minimizes the associated corrosion problems and prevents the occurrence of waste acid.

It has also been found that, based on the ACH use, a higher yield of methacrylic acid is achieved.

BRIEF DESCRIPTION OF THE FIGURE

FIG. 1 depicts a schematic showing one embodiment of the inventive process with emphasis on the hydrolysis of the methacrylic esters to form methacrylic acid.

DETAILED DESCRIPTION OF THE INVENTION

The preparation of acetone cyanohydrin from hydrogen cyanide and acetone is known and is described, for example, in EP 1 171 420 and DE 102006058250. The subsequent conversion of acetone cyanohydrin to methacrylamides is described, for example, in WO 2008/068064.

The esterification of methacrylamide in the presence of methanol to give methyl methacrylate is likewise prior art and is described, for example, in WO 2008/068063. The publications cited here form part of the disclosure.

Step a) Preparation of Acetone Cyanohydrin

Acetone cyanohydrin, α-hydroxyisobutyronitrile, is the most important starting material for all derivatives of methacrylic acid and in particular the esters thereof. In industry, acetone cyanohydrin is prepared by base-catalysed addition of hydrogen cyanide (hydrocyanic acid) onto acetone. In the neutral and particularly in the alkaline range, acetone cyanohydrin is in equilibrium with the starting components thereof. The commercial processes utilize predominantly liquid phase processes, which are performed either batchwise or continuously in the presence of catalysts, such as sodium hydroxide solution, potassium hydroxide solution, potassium carbonate, sodium acetate/acetic acid, pyridine/acetic acid and anion exchange resins, at temperatures below 40° C. Reference is made by way of example to the Rohm and Haas process (see Ullmann's Encyclopedia of Industrial Chemistry $5^{th}$ ed. (1985), pages 91-92). In this process, liquid hydrocyanic acid, acetone and a basic catalyst are introduced continuously into a reactor and then the reaction mixture, after stabilization with sulphuric acid and filtration of the catalyst, is freed by a two-stage distillation first of unconverted hydrocyanic acid and acetone, and then of water. The offgases from the first distillation stage are recycled into the reactor; pure stabilized acetone cyanohydrin is withdrawn at the bottom of the second distillation stage. A disadvantage of this process is that hydrogen cyanide has to be liquefied from a gas comprising hydrogen cyanide, for example a crude gas from the BMA or Andrussow process for preparation of hydrogen cyanide.

It is also known that, instead of liquefied hydrocyanic acid, a gas mixture comprising hydrogen cyanide and inert gases can be used, for example coking oven gases, in a process for preparing acetone cyanohydrin. In the process of Reinpreussen AG (see Ullmann's Encyklopedie der Technischen Chemie [Ullmann's Encyclopaedia of Industrial Chemistry], 4th edition, volume 7, pages 34-35) coking oven gases comprising hydrogen cyanide, after potash scrubbing, are scrubbed continuously in countercurrent with acetone containing 10% water and the reaction to give acetone cyanohydrin is performed in the presence of a basic catalyst in two gas scrubbing columns connected in series; the workup of the reaction mixture comprising acetone cyanohydrin comprises two acetone columns and two columns for purification of the acetone cyanohydrin.

EP 1 171 420 discloses a process for continuously preparing acetone cyanohydrin, comprising reaction of hydrogen cyanide with acetone in the presence of a basic catalyst and acetone cyanohydrin in a gas-liquid reactor, to which a gas mixture comprising hydrogen cyanide and inert gases, and acetone, are supplied continuously and from which a liquid phase comprising acetone cyanohydrin and a gas phase comprising the inert gases are removed, and distillative separation of volatile constituents from the liquid phase, which is characterized in that the gas phase removed from the reactor is freed of unconverted hydrogen cyanide and acetone in a gas scrubber charged with a solvent which boils at 100 to 200° C. (standard pressure) or with stabilized pure acetone cyanohydrin, and the resulting scrubbed phase is supplied to the gas-liquid reactor. In this process, preference is given to using a crude BMA gas or a crude Andrussow gas. The gas mixture resulting from said customary processes for preparing hydrogen cyanide can be used as such or after acid scrubbing. The crude gas from the BMA process, in which essentially hydrocyanic acid and hydrogen are formed from methane and ammonia, contains, according to Ullmann's Encyclopedia of Technical Chemistry, $5^{th}$ ed. (1987), vol. A8, p. 161-163, typically 22.9% by volume of HCN, 71.8% by volume of $H_2$, 2.5% by volume of $NH_3$, 1.1% by volume of $N_2$ and 1.7% by volume of $CH_4$.

In the known Andrussow process, hydrocyanic acid and water are formed from methane, ammonia and atmospheric oxygen. The crude gas of the Andrussow process contains, in the case of use of atmospheric oxygen as the oxygen source, according to the document cited above, typically 8% by volume of HCN, 22% by volume of $H_2$, 46.5% by volume of $N_2$, 15% by volume of $H_2O$, 5% by volume of CO, 2.5% by volume of $NH_3$ and 0.5% by volume each of $CH_4$ and $CO_2$.

The crude acetone cyanohydrin (crude ACH) drawn off from the reactor is worked up in the manner known to those skilled in the art. First, the crude ACH is stabilized by addition of an acid, then the low boilers HCN, acetone and water are distilled off in one or more stages. An appropriate configuration for workup of the crude ACH is evident from EP 0 421 237.

In the context of a further process element which can be used in connection with the present invention, acetone cyanohydrin which has been obtained in a preceding stage, for example from the reaction of acetone with hydrocyanic acid, can be subjected to a distillative workup.

Step b) Conversion of Acetone Cyanohydrin to Methacrylamide

In a further process step, the acetone cyanohydrin prepared in the first step is subjected to a hydrolysis. At various temperature levels, after a series of reactions, the product formed is methacrylamide.

The conversion is brought about in a manner known to those skilled in the art by a reaction between concentrated sulphuric acid and acetone cyanohydrin. The conversion is exothermic, and so, for example, the reaction can be controlled by removing heat of reaction from the system.

Step c) Esterification of Methacrylamide in the Presence of Methanol to Give Methyl Methacrylate A further step of the invention is the alcoholysis of methacrylamide to the corresponding methacrylic esters. Suitable in principle for this purpose are any alkanols having 1 to 4 carbon atoms, which may be linear or branched, saturated or unsaturated, particular preference being given to methanol. These alkanols can likewise be used together with methacrylic esters, which is the case especially for transesterifications. The amount of amide solution and of alkanol is regulated such that there is a total molar ratio of amide to alkanol of 1:1.4 to 1:1.6. The alkanol can be distributed over the tank cascade such that the molar ratio is 1:1.1 to 1:1.4 in the first reactor, and molar ratios of 1:0.05 to 1:0.3 are established in the downstream reaction stages, based on the overall amide stream. The alkanol fed into the esterification may be composed of "fresh alkanol" and alkanol from recycling streams of the workup stages and, if required, also of recycling streams from the downstream processes in the integrated production system.

Since methacrylic esters have a strong tendency to polymerize, it is advantageous to ensure that such a polymerization is prevented.

In order to prevent the polymerization, it may be advantageous to conduct optimization of the flow. Firstly, the flow rate of the methacrylic ester can be optimized. In addition, it may be advantageous to admix the stream of methacrylic ester with suitable stabilizers in such a way that polymerization is substantially suppressed.

The MMA obtained in the esterification and subsequent prepurification or the methacrylic ester obtained are subsequently sent to a further treatment. The remaining residual material resulting from the esterification is dilute sulphuric acid, which can likewise be sent to a further utilization.

Purification of the Methacrylic Ester

In principle, crude methacrylic acid or a crude methacrylic ester can be subjected to a further purification in order to obtain a very substantially pure product. This alternative process step for purification may, for example, have one stage. However, it has been found to be advantageous in many cases when such a purification comprises at least two stages. After a prepurification by removal of the low-boiling constituents, a subsequent main purification by means of distillation is advisable for removal of the high-boiling constituents.

Step d) Hydrolysis of the Methacrylic Ester to Methacrylic Acid

A further process step of the invention is the hydrolysis of the methacrylic ester described above to methacrylic acid. The reactants in this process step (methacrylic ester and water) are combined and the reaction mixture is brought to the suitable temperature. The reaction conditions with regard to pressure and temperature should be matched in the manner known to those skilled in the art to the alcohol component of the methacrylic ester used. Particular preference is given to using methyl methacrylate in the process according to the invention. The hydrolysis is effected in the presence of heterogeneous catalysts. Suitable catalysts are selected from the group of the zeolites, ion exchange resins and amorphous acid catalysts.

A multitude of suitable catalysts can be found by the person skilled in the art in EP 1 352 891. Particular preference is given to cationic ion exchange resins. Suitable catalysts are ion exchangers such as Lewatit K1221, from Lanxess AG, Lewatit K2629, from Lanxess AG, Dowex CM-4, from Dow Chemical, Dowex M-31, from Dow Chemical, Dowex M-3 MS, from Dow Chemical, Amberlyst 39 Wet, from Rohm & Haas, Amberlyst CSP2, from Rohm & Haas, Amberlyst CSP3, from Rohm & Haas, DIAION PK208, from Mitsubishi Chemicals, DIAION PK216, from Mitsubishi Chemicals, DIAION PK228, from Mitsubishi Chemicals. A very particularly preferred catalyst is Lewatit K2431, from Lanxess AG.

It has been found that, depending on the polymerization tendency of the monomer mixture used, the nature of the catalyst and/or the size of the catalyst bed, flow through the catalyst bed from the top or bottom is advantageous. Preference is given to inflow from the bottom.

The hydrolysis of the methacrylic esters is performed at temperatures between 50 and 200° C., preferably between 70 and 150° C., more preferably at 90-120° C. and most preferably at 100 to 110° C.

Preference is given at the same time to working at elevated pressure, preferably under a pressure of 0.1-9 bar gauge, more preferably at 2-4 bar gauge. The pressure in the reactor is adjusted in such a way that this pressure is measured at the reactor outlet.

The reactant stream of methacrylic ester and water preferably has a composition where the ratio of methacrylic ester to water is between 0.5 and 5, preferably between 1 and 4, more preferably between 1.5 and 3.

The residence time (calculated on the basis of the superficial catalyst volume) is 10-120 min, preferably 30-90 min, more preferably 45-75 min.

The mass or volume ratio of circulation stream (2) to feed stream (1) is preferably 5 to 50, more preferably 15 to 30.

Process Description

Step a) Provision of Acetone Cyanohydrin

The provision of acetone cyanohydrin is performed by commonly known processes (see, for example, Ullmanns Enzyklopadie der technischen Chemie, 4th edition, volume 7). The reactants used are acetone and hydrocyanic acid. The reaction is an exothermic reaction. In order to counteract decomposition of the acetone cyanohydrin formed in this reaction, the heat of reaction is typically removed by a suitable apparatus. The reaction can in principle be conducted as a batch process or as a continuous process; if a continuous mode of operation is preferred, the reaction is frequently performed in a loop reactor with a corresponding setup.

A main feature of a mode of operation which leads to the desired product in high yields is that the reaction product is cooled at sufficient reaction time, and the reaction equilibrium is shifted in the direction of the reaction product. In addition, the reaction product, for the benefit of the overall yield, is frequently admixed with an appropriate stabilizer in order to prevent decomposition to the starting materials in the course of later workup.

The mixing of the acetone and hydrocyanic acid reactants can in principle be effected in any desired manner. The method of mixing depends more particularly on whether a discrete mode of operation, for example in a batch reactor, or a continuous mode of operation, for example in a loop reactor, is selected.

In principle, it may be advantageous when the acetone is fed into the reaction via a reservoir vessel possessing a scrubbing tower. Vent lines which conduct output air comprising acetone and hydrocyanic acid can thus be conducted, for example, through this reservoir vessel. In the scrubbing tower connected to the reservoir vessel, the output air escaping from the reservoir vessel can be scrubbed with acetone, as a result of which hydrogen cyanide is removed from the output air and recycled into the process. For this purpose, for example, a portion of the amount of acetone introduced into the reaction from the reservoir vessel is conducted in a substream through a cooler, preferably through a brine cooler, into the top of the scrubbing tower and the desired result thus achieved.

According to the size of the amount of end products to be produced, it may be advantageous to supply the acetone to the reaction from more than just one reservoir vessel. In this case, each of the two or more reservoir vessels may bear a corresponding scrubbing tower. However, it is in many cases sufficient when only one of the reservoir vessels is equipped with a corresponding scrubbing tower. In this case, however, it is often advisable for corresponding pipes which conduct output air and which can transport acetone and hydrogen cyanide to be conducted through this vessel or through this scrubbing tower.

The temperature of the acetone in the reservoir vessel may in principle be within an essentially arbitrary range, provided that the acetone at the corresponding temperature is in the liquid state. Advantageously, the temperature in the reservoir vessel is, however, 0 to 20° C.

In the scrubbing tower, the acetone used for scrubbing is cooled by means of a corresponding cooler, for example by means of a plate cooler with brine, to a temperature of 0 to 10° C. The temperature of the acetone on entry to the scrubbing tower is therefore, for example, 2 to 6° C.

The hydrocyanic acid required in the reaction can be introduced into the reactor either in liquid or gaseous form. It may, for example, be crude gas from the BMA process or from the Andrussow process.

The hydrogen cyanide can, for example, be liquefied, for example by the use of a corresponding cooling brine. Instead of liquefied hydrocyanic acid, it is possible to use coking oven gas. For example, hydrogen cyanide-containing coking oven gases, after scrubbing with potash, are scrubbed continuously in countercurrent with acetone containing 10% water, and the reaction to give acetone cyanohydrin can be performed in the presence of a basic catalyst in two gas scrubbing columns connected in series.

In a further embodiment, a gas mixture comprising hydrogen cyanide and inert gases, especially a crude gas from the BMA process or from the Andrussow process, can be reacted with acetone in the presence of a basic catalyst and acetone cyanohydrin in a gas-liquid reactor.

In the process described here, preference is given to using a crude BMA gas or a crude Andrussow gas. The gas mixture resulting from the abovementioned customary processes for preparation of hydrogen cyanide can be used as such or after an acid scrubbing. The crude gas from the BMA process, in which essentially hydrocyanic acid and hydrogen are formed from methane and ammonia, contains typically 22.9% by volume of HCN, 71.8% by volume of $H_2$, 2.5% by volume of $NH_3$, 1.1% by volume of $N_2$, 1.7% by volume of $CH_4$. In the known Andrussow process, hydrocyanic acid and water are formed from methane and ammonia and atmospheric oxygen. The crude gas of the Andrussow process contains, when oxygen is used as the oxygen source, typically 8% by volume of HCN, 22% by volume of $H_2$, 46.5% by volume of $N_2$, 15% by volume of $H_2O$, 5% by volume of CO, 2.5% by volume of $NH_3$ and 0.5% by volume each of $CH_4$ and $CO_2$.

In the case of use of a non-acid-scrubbed crude gas from the BMA or Andrussow process, the ammonia present in the crude gas frequently acts as a catalyst for the reaction. Since the ammonia present in the crude gas frequently exceeds the amount required as a catalyst and can therefore lead to high losses of sulphuric acid used for stabilization, such a crude gas is often subjected to acid scrubbing in order to eliminate ammonia therefrom. In the case of use of such an acid-scrubbed crude gas, it is then necessary, however, to add a suitable basic catalyst to the reactor in a catalytic amount. In principle, known inorganic or organic basic compounds can function as the catalyst.

Hydrogen cyanide in gaseous or liquid form, or a gas mixture comprising hydrogen cyanide, and acetone are fed continuously to a loop reactor in the continuous mode of operation. The loop reactor comprises at least one means for supply of acetone or two or more such means, at least one means for supply of liquid or gaseous hydrocyanic acid, or two or more such means, and at least one means for supply of a catalyst.

Suitable catalysts are in principle any alkaline compounds, such as ammonia, sodium hydroxide solution or potassium hydroxide solution, which can catalyse the conversion of acetone and hydrocyanic acid to acetone cyanohydrin. It has been found to be advantageous, however, when the catalyst used is an organic catalyst, especially an amine. Suitable examples are secondary or tertiary amines, such as diethylamine, dipropylamine, triethylamine, tri-n-propylamine and the like.

A loop reactor usable in the process element described additionally has at least one pump, or two or more pumps, and at least one mixing apparatus, or two or more such mixing apparatuses.

Suitable pumps are in principle all pumps suitable for ensuring the circulation of the reaction mixture in the loop reactor.

Suitable mixing apparatuses are both mixing apparatuses with moving elements and what are called static mixers, in which immobile flow resistors are provided. Corresponding mixers may consist of plastic or metal. Suitable plastics are, for example, PVC, PP, HDPE, PVDF, PFA or PTFE. Metal mixers may consist, for example, of nickel alloys, zirconium, titanium and the like. Likewise suitable are, for example, rectangular mixers.

The catalyst is preferably added in the loop reactor downstream of the pump and upstream of any mixing element provided in the loop reactor. Catalysts are used in the reaction described, for example, in such an amount that the overall reaction is conducted at a pH of not more than 8, especially not more than 7.5 or 7. It may be preferable when the pH in the reaction varies within a range from 6.5 to 7.5, for example 6.8 to 7.2.

It is also possible in the process described, as an alternative to the addition of the catalyst to the loop reactor downstream of the pump and upstream of any mixing apparatus, to feed the catalyst into the loop reactor together with the acetone. In such a case, it may be advantageous when appropriate mixing of acetone and catalyst is ensured prior to feeding into the loop reactor. Corresponding mixing can be effected, for example, by the use of a mixer with moving parts or by use of a static mixer.

When, in the process described, a continuous mode is selected as the method of operation in a loop reactor, it may be appropriate to examine the state of the reaction mixture by instantaneous or continual analyses. This gives the advantage that it is possible to react rapidly even to any changes in state in the reaction mixture. In addition, it is thus possible, for example, to meter the reactants with very high accuracy, in order to minimize yield losses.

Corresponding analysis can be effected, for example, by sampling in the reactor loop. Suitable analysis methods are, for example, pH measurement, measurement of exothermicity, or measurement of the composition of the reaction mixture by suitable spectroscopic methods.

Especially for the purposes of conversion monitoring, quality aspects and safety, it has frequently been found to be useful to determine the conversion in the reaction mixture via the heat released from the reaction mixture and to compare it with the heat released theoretically.

In the case of suitable selection of the loop reactor, the actual reaction can in principle be effected in the tube systems arranged within the loop reactor. Since the reaction, however, is exothermic, in order to avoid yield losses, it is possible to ensure sufficient cooling or sufficient removal of the heat of reaction. It has frequently been found to be advantageous when the reaction proceeds within a heat exchanger, preferably within a shell and tube heat exchanger. According to the amount of product to be produced, the capacity of a corresponding heat exchanger can be selected differently. For industrial scale processes, especially heat exchangers with a capacity of 10 to 40 m$^3$ have been found to be particularly suitable. The shell and tube heat exchangers used with preference are heat exchangers which have a tube system through which liquid flows in a shell through which liquid flows. According to the tube diameter, packing density, etc., the heat transfer between the two liquids can be adjusted correspondingly. It is possible in principle in the process described to conduct the reaction such that the reaction mixture is conducted through the heat exchanger in the tube system itself and the reaction takes place within the tube system, the heat being removed from the tube system to the shell liquid.

It has been found, however, likewise to be practicable and in many cases to be advisable to conduct the reaction mixture through the shell of the heat exchanger, while the liquid used for cooling circulates within the tube system. In many cases, it has been found to be advantageous when the reaction mixture in the shell is distributed by means of flow resistors, preferably baffles, to achieve a higher residence time and better mixing.

The ratio of shell volume to the volume of the tube system may, according to the design of the reactor, be 10:1 to 1:10; the volume of the shell is preferably greater than the volume of the tube system (based on the contents of the tubes).

The heat removal from the reactor with an appropriate coolant, for example, with water, is adjusted such that the reaction temperature is within a corridor at 25 to 45° C., especially at 30 to 38° C., especially at 33 to 35° C.

A product is removed continuously from the loop reactor. The product has a temperature in the range of the abovementioned reaction temperatures, for example a temperature of 35° C. The product is cooled by means of one or more heat exchangers, especially by means of one or more plate heat exchangers. For example, brine cooling is used. The temperature of the product after cooling should be 0 to 10° C., especially 1 to 5° C. The product is preferably transferred to a storage vessel which has a buffer function. In addition, the product in the storage vessel can be cooled further, for example by constant removal of a substream from the storage vessel to a suitable heat exchanger, for example, to a plate heat exchanger, or be kept at a suitable storage temperature. It is entirely possible that a postreaction can take place in the storage vessel.

The product can in principle be recycled into the storage vessel in any desired manner. However, it has been found to be advantageous in some cases for the product to be recycled into the storage vessel via a system composed of one or more nozzles, such that corresponding mixing of the stored product takes place within the storage vessel.

Product continues to be removed continuously from the storage vessel to a stabilization vessel. The product is admixed therein with a suitable acid, for example with H$_2$SO$_4$. This deactivates the catalyst and adjusts the reaction mixture to a pH of 1 to 3, especially 2. A suitable acid is especially sulphuric acid, for example sulphuric acid with a content of 90 to 105%, especially of 93 to 98% H$_2$SO$_4$.

The stabilized product is withdrawn from the stabilization vessel and transferred to the purification stage. A portion of the stabilized product withdrawn can be recycled into the stabilization vessel, for example in such a way that sufficient mixing of the vessel is ensured by means of a system composed of one or more nozzles.

In a further process element which can be used in connection with the present invention, acetone cyanohydrin is subjected to a distillative workup. This involves freeing the stabilized crude acetone cyanohydrin of low-boiling constituents by means of an appropriate column. A suitable distillation process can be conducted, for example, using only one column. It is, however, likewise possible to use a combination of two or more distillation columns, also in combination with a falling-film evaporator, in a corresponding purification of crude acetone cyanohydrin. It is additionally possible to combine two or more falling-film evaporators, or else two or more distillation columns, with one another.

The crude acetone cyanohydrin generally arrives from the storage at the distillation with a temperature of 0 to 15° C., for example a temperature of 5 to 10° C. In principle, the crude acetone cyanohydrin can be introduced directly into the column. However, it has been found to be useful in some cases when the crude cool acetone cyanohydrin first of all takes on a portion of the heat of the product already purified by distillation by means of a heat exchanger. Therefore, in a further embodiment of the process described here, the crude acetone cyanohydrin is heated to a temperature of 60 to 80° C. by means of a heat exchanger.

The distillative purification of the acetone cyanohydrin is effected by means of a distillation column or a rectification column having more than 10 trays, or by means of a cascade of two or more correspondingly suitable distillation columns. The column bottom is preferably heated with steam. It has been found to be advantageous when the bottom temperature does not exceed a temperature of 140° C.; it has been possible to achieve good yields and good purification when the bottom temperature is not greater than 130° C. or not higher than 110° C. The temperature figures are based on the wall temperature of the column bottoms.

The crude acetone cyanohydrin is supplied to the column body in the upper third of the column. The distillation is performed preferably at reduced pressure, for example at a pressure of 50 to 900 mbar, especially 50 to 250 mbar and with good results between 50 and 150 mbar.

At the top of the column, gaseous impurities, especially acetone and hydrocyanic acid, are withdrawn; the gaseous substances removed are cooled by means of a heat exchanger or a cascade of two or more heat exchangers. Preference is given here to using brine cooling with a temperature of 0 to 10° C. This gives the gaseous constituents of the vapours the opportunity to condense. The first condensation stage can take place, for example, at standard pressure. However, it is likewise possible and has been found to be advantageous in some cases when this first condensation stage is effected under reduced pressure, preferably at the prevailing pressure in the distillation. The condensate is passed on into a cooled collecting vessel and collected there at a temperature of 0 to 15° C., especially at 5 to 10° C.

The gaseous compounds which do not condense in the first condensation step are removed from the reduced pressure space by means of a vacuum pump. It is possible here in principle to use any vacuum pump. However, it has been found to be advantageous in many cases to use a vacuum pump which, due to its design, does not lead to the introduction of liquid impurities into the gas stream. Preference is given here, therefore, to using, for example, dry-running vacuum pumps.

The gas stream which escapes on the pressure side of the pump is conducted through a further heat exchanger, which is preferably cooled with brine at a temperature of 0 to 15° C. Constituents which condense here are likewise collected in the collecting vessel which already collects the condensates obtained under vacuum conditions. The condensation conducted on the pressure side of the vacuum pump can be effected, for example, by means of a heat exchanger, but also with a cascade of two or more heat exchangers arranged in series and in parallel. After this condensation step, gaseous substances remaining are removed and supplied to any further utilization, for example to a thermal utilization.

The collected condensates can likewise be utilized further in any desired manner. However, it has been found to be extremely advantageous on economic grounds to recycle the condensates into the reaction for preparation of acetone cyanohydrin. This is preferably done at one or more points which enable access to the loop reactor. The condensates may in principle have any composition, provided that they do not disrupt the preparation of the acetone cyanohydrin. In many cases, the predominant amount of the condensate will, however, consist of acetone and hydrocyanic acid, for example in a molar ratio of 2:1 to 1:2, frequently in a ratio of 1:1.

The acetone cyanohydrin obtained from the bottom of the distillation column is first cooled to a temperature of 40 to 80° C. by the cold crude acetone cyanohydrin supplied by means of a first heat exchanger. Subsequently, the acetone cyanohydrin is cooled to a temperature of 30 to 35° C. by means of at least one further heat exchanger, and optionally sent to intermediate storage.

Overall, it has been found to be advantageous in some cases when the acetone cyanohydrin is freed in a rectification column at least of impurities having a boiling point of more than −5° C. and less than 100° C., for example more than 0° C. and less than 90° C., and these impurities are recycled into the reaction for preparation of acetone cyanohydrin. The corresponding process variant is advantageously performed with the aid of an apparatus which has a rectification column for removal of constituents having a boiling point of more than −5° C. and less than 100° C. from the acetone cyanohydrin prepared, and the rectification column is in fluid-conducting connection with the plant element for preparation of acetone cyanohydrin such that the constituents removed can be recycled into the reaction for preparation of acetone cyanohydrin.

Step b) Conversion of Acetone Cyanohydrin to Methacrylamide

In a further process step, the acetone cyanohydrin prepared in the first step is subjected to a hydrolysis. The conversion is effected in a manner known to those skilled in the art, by a reaction between concentrated sulphuric acid and acetone cyanohydrin.

The reaction here too can again be performed in a batchwise process or in a continuous process. The latter has been found to be advantageous in many cases. When the conversion is performed in a continuous process, the use of loop reactors has been found to be useful. The conversion can be effected, for example, in only one loop reactor. However, it may be advantageous when the conversion is performed in a cascade of two or more loop reactors.

A suitable loop reactor has, in the process described, one or more feed points for acetone cyanohydrin, one or more feed points for concentrated sulphuric acid, one or more gas separators, one or more heat exchangers and one or more mixers.

The hydrolysis of acetone cyanohydrin with sulphuric acid to give methacrylamide is exothermic, as already described. The heat of reaction obtained in the reaction can, however, advantageously be removed from the system at least to such an extent that a maximization of yield can be achieved, since the yield falls with increasing temperature in the reaction. It is possible in principle to achieve rapid and comprehensive removal of the heat of reaction with appropriate heat exchangers. However, it may be advantageous not to cool the mixture too much, since sufficient heat transfer is required for corresponding exchange in the heat exchangers. Since the viscosity of the mixture rises with falling temperature, circulation in the loop reactor can become more difficult in the event of excessive cooling. In this case, it is possible that sufficient removal of the reaction energy from the system can no longer be ensured.

In addition, excessively low temperatures in the reaction mixture can lead to crystallization of constituents of the reaction mixture in the heat exchangers. This can further worsen the heat transfer, which may cause a decline in yield. In addition, excessive cooling may have the result that the loop reactor cannot be charged with the optimal amounts of reactants, and so the efficiency of the process may suffer.

In a further configuration of the invention, a portion, for example two thirds to three quarters, of the volume flow from a stream of acetone cyanohydrin can be introduced into a first loop reactor. Such a first loop reactor may have one or more heat exchangers, one or more pumps, one or more mixing elements and one or more gas separators. The circulation flow rates running through the first loop reactor are, for example, in the range from 100 to 450 $m^3/h$, preferably within a range from 200 to 400 $m^3/h$ and additionally preferably within a range from 250 to 350 $m^3/h$. In at least one further loop reactor which follows the first loop reactor, the circulation flow rates are preferably within a range from 40 to 450 $m^3/h$, more preferably within a range from 50 to 400 $m^3/h$ and additionally preferably within a range from 60 to 350 $m^3/h$. In addition, a preferred temperature difference over the heat exchanger is 1 to 10° C., more preferably 2 to 7° C.

The acetone cyanohydrin can in principle be supplied to the loop reactor at any point. However, it has been found to be advantageous when the supply is effected into a mixing element, for example into a mixer with moving parts or a static mixer. The sulphuric acid is advantageously supplied upstream of the acetone cyanohydrin addition. Otherwise, however, it is likewise possible to introduce the sulphuric acid into the loop reactor at any point.

The ratio of the reactants in the loop reactor is controlled, for example, such that an excess of sulphuric acid is present. The excess of sulphuric acid may, based on the molar ratio of the constituents, be 1.8:1 to 3:1 in the first loop reactor and 1.3:1 to 2:1 in the last loop reactor.

In some cases, it has been found to be advantageous to conduct the reaction in the loop reactor with such an excess of sulphuric acid. The sulphuric acid can serve here, for example, as a solvent and keep the viscosity of the reaction mixture low, as a result of which higher removal of heat of reaction and a lower temperature of the reaction mixture can be ensured. This can give rise to distinct yield advantages. The temperature in the reaction mixture is 90 to 120° C., for example 95 to 115° C.

The heat removal can be ensured by means of one or more heat exchangers in the loop reactor. It has often been found to be advantageous when the heat exchangers possess a suitable sensor system for adjustment of the cooling performance, in order to prevent excessive cooling of the reaction mixture for the reasons mentioned above. For example, it may be advantageous to measure the heat transfer instantaneously or continuously in the heat exchanger or in the heat exchangers, and to match the cooling performance of the heat exchangers thereto. This can be accomplished, for example, by means of the coolant itself. It is also likewise possible, by appropriate variation of the addition of the reactants and by the production of more heat of reaction, to achieve corresponding heating of the reaction mixture. A combination of the two options is also conceivable. The loop reactor should additionally possess at least one gas separator. The gas separator is used firstly to withdraw product formed continuously from the loop reactor. Secondly, gases formed in the course of the reaction can thus be removed from the reaction space. The gas formed is principally carbon monoxide. The product withdrawn from the loop reactor is preferably transferred into a second loop reactor. In this second loop reactor, the reaction mixture comprising sulphuric acid and methacrylamide, as obtained by the reaction in the first loop reactor, is reacted with the remaining substream of acetone cyanohydrin. The excess of sulphuric acid from the first loop reactor, or at least a portion of the excess sulphuric acid, reacts here with the acetone cyanohydrin to form further methacrylamide. The performance of the reaction in two or more loop reactors has the advantage that, due to the sulphuric acid excess in the first loop reactor, the pumpability of the reaction mixture and hence the heat transfer, and ultimately the yield, are improved. In the second loop reactor are again arranged at least one mixing element, at least one heat exchanger and at least one gas separator. The reaction temperature in the second loop reactor is likewise 90 to 120° C.

The problem of pumpability of the reaction mixture, of heat transfer and of a minimum reaction temperature occurs just as much in every further loop reactor as in the first. Therefore, the second loop reactor also advantageously has a heat exchanger, the cooling performance of which can be regulated by a corresponding sensor system.

The acetone cyanohydrin is in turn supplied in a suitable mixing element, preferably in a static mixer.

The product is withdrawn from the gas separator of the second loop reactor and heated to a temperature of 140 to 180° C. to complete the conversion and to form methacrylamide.

The heating is preferably conducted in such a way that the maximum temperature is achieved only for a very short period, for example for a time of 1-30 min, especially for a time of 2-8 and preferably 3-5 min. This can in principle be effected in any desired apparatuses for achievement of such a temperature for such a short period. For example, the energy can be supplied in a conventional manner, through electrical energy or through steam. It is, however, likewise possible to supply the energy through electromagnetic radiation, for example through microwaves.

It has been found to be advantageous in various cases for the heating step to be effected in a heat exchanger with two-stage or multistage arrangement of tube coils, which may preferably be present in an at least double, opposing arrangement. In this case, the reaction mixture is heated rapidly to a temperature of 140 to 180° C.

The heat exchanger can be combined, for example, with one or more gas separators. For example, it is possible to conduct the reaction mixture through a gas separator after it has left the first tube coil in the heat exchanger. This can remove, for example, gaseous components formed during the reaction from the reaction mixture. It is likewise possible to treat the reaction mixture with a gas separator after it leaves the second coil. It may additionally be found to be advantageous to treat the reaction mixture with a gas separator at both points, both after it leaves the first tube coil and after it leaves the second tube coil.

The amide solution thus obtainable generally has a temperature of more than 100° C., typically a temperature of 140 to 180° C.

The gaseous compounds obtained in the course of amidation can in principle be disposed of in any desired manner or be sent to further processing. It may, however, be advantageous in some cases when the corresponding gases are combined in a transport pipe in such a way that they can optionally be subjected to pressure, for example to steam pressure, either continuously or as required, and thus transported onward.

In a further embodiment of the invention, it has been found to be advantageous in some cases for gaseous products obtained in the preparation of methacrylamide, in the course of further transport, to be introduced into the reaction mixture of the esterification outlined hereinafter. Such an introduction can in principle be effected at any point in the esterification. It is often advantageous, however, especially when an esterification is effected in several tanks, to introduce the gaseous products obtained into the reaction mixture of the esterification, which is present in a first tank. The introduction of the gaseous products obtained can be configured, for example, such that the gases contacted with steam are introduced into a tank such that they ensure at least local mixing of the tank contents or heating of the tank contents or an essentially constant temperature of the tank contents or a combination of two of the elements mentioned.

Step c) Esterification of Methacrylamide in the Presence of Alcohols to Give Methacrylic Esters A further step of the invention is the alcoholysis of methacrylamide to the corresponding methacrylic esters. This reaction can be performed in one or more heated, for example steam-heated, tanks. It has been found to be advantageous in many cases when the esterification is performed in at least two successive tanks, but, for example, also in three or four or more successive tanks. In this case, a solution of methacrylamide is introduced into the tank or into the first tank of a cascade of tanks comprising two or more tanks.

It is frequently preferable to perform an esterification reaction of this kind with a cascade of two or more tanks. Reference shall therefore be made hereinafter exclusively to this variant.

In the context of the invention described here, it is possible, for example, to feed an amide solution as obtainable from the amidation reaction described here into a first tank. The tank is heated, for example, with steam. The amide solution supplied generally has an elevated temperature, for example, a temperature of 100 to 180° C., essentially corresponding to the output temperature of the amide solution from the amidation reaction presented above. Additionally supplied to the tanks is an alkanol, which can be used for esterification.

In principle, any alkanols having 1 to 4 carbon atoms are suitable here, and these may be linear or branched, saturated or unsaturated, particular preference being given to methanol. These alkanols can likewise be used together with methacrylic esters, which is the case especially for transesterifications.

The tank is additionally charged with water, such that there exists an overall water concentration in the tank of 13 to 26% by weight, especially 18 to 20% by weight.

The amount of amide solution and of alkanol is regulated such that there exists an overall molar ratio of amide to alkanol of 1:1.4 to 1:1.6. The alkanol can be distributed over the tank cascade such that the molar ratio in the first reactor is 1:1.1 to 1:1.4, and molar ratios of 1:0.05 to 1:0.3 are established in the downstream reaction stages, based on the overall amide stream. The alkanol supplied to the esterification may be composed of "fresh alkanol" and alkanol from recycling streams of the workup stages, and, if required, also from recycling streams of the downstream processes of the integrated production system.

The first tank can be charged with water in principle in such a way that water is supplied to the tank from any source, provided that this water does not have any constituents which could adversely affect the esterification reaction or the downstream process stages. For example, the tank may be supplied with demineralized water or spring water. However, it is likewise possible to supply a mixture of water and organic compounds to the tank, as obtained, for example, in the purification of methacrylic acid or methacrylic esters. In a preferred embodiment of the process presented here, the tanks are charged at least partly with a mixture of water and such organic compounds.

When a cascade of two or more tanks is used in the esterification reaction, the gaseous substances formed, especially the methacrylic ester, can in principle be drawn off from each tank individually and sent to a purification. However, it has been found to be advantageous in some cases when, in the case of a cascade of two or more tanks, the gaseous products from the first tank are first fed into the second reaction tank without supplying the gaseous compounds from the first tank directly to a purification. This procedure offers the advantage that the evolution of foam, which is frequently significant in the first tank, need not be countered by complex defoaming apparatus. In the case of cascading of the gaseous substances from the first tank into the second tank, the foam which is formed in the first tank and may be entrained simply also enters the reaction space of the second tank. Since foam formation therein is generally much lower, there is thus no need for defoaming apparatus.

The second tank arranged downstream of a first tank then firstly accommodates the overflow of the first tank; secondly, it is fed with the gaseous substances formed in the first tank or present in the first tank. The second tank and any downstream tanks are likewise charged with methanol. It is preferable here that the amount of methanol decreases by at least 10% from tank to tank, based in each case on the preceding tank. The water concentration in the second tank and in the further tanks may differ from that in the first tank, but the difference in concentration is often small.

The vapours arising in the second tank are removed from the tank and introduced into the bottom of a distillation column.

When the esterification is performed with a cascade of three or more tanks, the overflow of the second tank in each case is transferred into a third tank, and the overflow of the third tank, if appropriate, is transferred into a fourth tank. The further tanks are likewise steam-heated. The temperature in tanks 3 and, if appropriate, 4 is preferably adjusted to from 120° C. to 140° C.

The vapours escaping from the tanks are introduced into a distillation column, and they are preferably introduced in the lower region of the distillation column. The vapours comprise an azeotropic mixture of carrier steam, methacrylic ester and alkanol, and, according to the alkanol used, have a temperature of 60 to 120° C., for example 70 to 90° C., in the case of use of methanol. In the distillation column, the methacrylic ester is separated in gaseous form from the vapour constituents which boil at higher temperatures. The high-boiling components (principally methacrylamide, hydroxyisobutyric ester and water) are recycled into the first reaction tank. The methacrylic ester formed is drawn off at the top of the column and cooled by means of a heat exchanger or a cascade of two or more heat exchangers. It has been found to be useful in some cases when the methacrylic ester is cooled by means of at least two heat exchangers, a first heat exchanger with water conducting the condensation and cooling to a temperature of 60 to 30° C., while a second, brine-cooled heat exchanger undertakes cooling from 5 to 15° C. A substream of the water-cooled condensate can be introduced as reflux to the columns to control the concentration in the column. However, it is equally possible to cool the methacrylic ester formed by means of a cascade of more than two heat exchangers. In this case, it is possible, for example, first to undertake cooling by means of two water-cooled heat exchangers connected in series, and then to achieve further cooling by means of a corresponding brine-cooled heat exchanger.

For example, it is possible in the process presented here to cool the methacrylic ester formed in the gaseous state by means of a first heat exchanger with water cooling. Both condensed and uncondensed substances are subsequently passed onward into a second heat exchanger where further condensation by means of water cooling takes place. At this point, it is possible, for example, to transfer gaseous substances to a separate brine-cooled heat exchanger. The condensate in this brine-cooled heat exchanger is subsequently added to the distillate stream, while the gaseous substances remaining can be utilized further or sent to disposal. The methacrylic ester condensate from the second water-cooled heat exchanger is then cooled in a water- or brine-cooled heat exchanger to a temperature of less than 15° C., preferably 8 to 12° C. The effect of this cooling step may be that the methacrylic ester formed has a much lower content of formic acid than would be the case without the corresponding cooling step. The cooled condensate is subsequently transferred into a phase separator. The organic phase (methacrylic ester) is separated here from the aqueous phase. The aqueous phase which, as well as water, may also have a content of organic compounds, especially alkanol, from the distillation step, can in principle be used further as desired. However, as already described above, it may be preferable to recycle this mixture of water and organic compounds back into the esterification process, by feeding it into the first reaction tank.

The organic phase removed is fed into a scrubber. The methacrylic ester is scrubbed therein with demineralized water. The aqueous phase which separates out and comprises a mixture of water and organic compounds, especially alkanol, can in turn in principle be used further as desired. However, it is advantageous on economic grounds to recycle this aqueous phase back into the esterification step, by feeding it, for example into the first tank.

Since methacrylic esters have a strong tendency to polymerize, it is advantageous in many cases to ensure in the course of alcoholysis of the methacrylamide that such polymerization is prevented.

In plants for preparation of methacrylic acid or methacrylic esters, polymerization often takes place when the streams have too low a flow rate, such that there can be local formation of calm zones in which contact between the polymerizable constituents and a polymerization initiator can be established over a prolonged period, which can subsequently lead to polymerization.

In order to avoid corresponding polymerization behaviour, it may be advantageous to conduct an optimization of the flow to the effect that, firstly, the flow rate of the streams at virtually all points in the system is so high that the number of calm zones is minimized. In addition, it may be advantageous to admix the streams with suitable stabilizers in such a way that polymerization is substantially suppressed.

For this purpose, in the process presented here, the streams can in principle be admixed with stabilizers such that virtually no polymerization takes place in the system itself. For this purpose, more particularly, the part of the plant in which the methacrylic esters are present in high concentration during or after the distillation is supplied with appropriate stabilizers.

For example, it has been found to be advisable to supply a stabilizer at the top of the distillation column to the stream of methacrylic ester drawn off there. In addition, it has been found to be advantageous to use a solution of stabilizer in methacrylic ester to purge those plant parts in which methacrylic acid or methacrylic ester circulates with a temperature of more than 20° C., preferably with a temperature in the range from 20 to 120° C. For example, a portion of the condensate obtained in the heat exchangers is recycled together with a suitable stabilizer into the top of the distillation column such that the top of the column is constantly sprayed on its inside with stabilized methacrylic ester or stabilized methacrylic acid. This is preferably accomplished in such a way that there cannot be any formation in the top of the column of calm zones where there is a risk of polymerization of methacrylic acid or methacrylic ester. The heat exchangers themselves can correspondingly likewise be charged with a stabilized solution of methacrylic acid or methacrylic ester, in such a way that no calm zones can be formed here either.

It has additionally been found to be advantageous in the process presented here, for example, for the carbon monoxide-containing offgases from preceding processes, especially from the amidation step, to be passed through the esterification plant together with steam. In this way, the gas mixture is purified once again to remove compounds which can be removed in solid form or in liquid form. Secondly, these are collected at a central point and can be sent to further utilization or disposal.

The MMA obtained or the methacrylic ester obtained in the esterification and subsequent prepurification are subsequently sent to a further treatment. The remaining residue which results from the esterification is dilute sulphuric acid, which can likewise be sent to further utilization.

Optionally, in the process according to the invention, it is also possible to use a process for prepurifying methacrylic ester as described in the process steps which follow. Advantageously, the purification comprises two stages. In a first prepurification, the low-boiling constituents of the product are removed. For this purpose, crude methacrylic ester is first transferred to a distillation column in which the low-boiling constituents and water can be removed. For this purpose, the crude methacrylic ester is supplied to a distillation column, the addition being performed in the upper half of the column. The column bottom is heated with steam, for example, so as to attain a wall temperature of 50 to 120° C. The purification is performed under reduced pressure. The pressure within the column in the case of the ester is preferably 100 to 600 mbar.

At the top of the column, the low-boiling constituents are removed. More particularly, these may, for example, be ethers, acetone and methyl formate. The vapours are subsequently condensed by means of one or more heat exchangers. It has been found to be useful in some cases, for example, first to perform a condensation by means of two water-cooled heat exchangers connected in series. However, it is likewise possible to use only one heat exchanger at this point. The heat exchangers are preferably operated in the vertical state to increase the flow rate and to prevent formation of stationary phases. A brine-cooled heat exchanger may be connected downstream of the water-cooled heat exchanger or the water-cooled heat exchangers, but it is also possible to connect a cascade of two or more brine-cooled heat exchangers downstream. In the cascade of heat exchangers, the vapours are condensed, provided with stabilizers and supplied, for example, to a phase separator. Since the vapours may also comprise water, any aqueous phase which occurs is disposed of or sent to further utilization. A possible example of a further utilization is recycling into an esterification reaction, for example into an esterification reaction as described above. In this case, the aqueous phase is preferably recycled into the first esterification tank.

The organic phase removed is fed as reflux into the top of the column. A portion of the organic phase can in turn be used to spray the tops of the heat exchangers and the top of the column. Since the organic phase removed is a phase admixed with stabilizer, it is thus firstly possible to effectively prevent the formation of calm zones. Secondly, the presence of the stabilizer brings about a further suppression of the polymerization tendency of the vapours removed.

The condensate stream obtained from the heat exchangers is additionally preferably admixed with demineralized water in such a way that, in the phase separator, a sufficient separating action can be achieved.

The gaseous compounds remaining after the condensation in the heat exchanger cascade can be subjected once again to a condensation using one or more further heat exchangers, preferably by means of steam ejectors as reduced pressure generators. It has been found to be advantageous on economic grounds for not only the gaseous substances from the prepurification to be condensed in such a postcondensation. For example, it is possible to supply such a postcondensation with further gaseous substances as arise from the main purification of methacrylic esters. The advantage of such a procedure lies in the fact that, for example, any proportion of methacrylic ester which has not been condensed in the main purification stage can thus be transferred once again into the purification column via the phase separator in the course of prepurification. For example, it is ensured that yield maximization can take place, and minimum losses of methacrylic ester occur. In addition, the suitable selection of the design and of the operation of these further heat exchangers allows the composition of the offgas leaving these heat exchangers, especially the content of low boilers, to be adjusted.

Due to the supply of water in the prepurification of the methacrylic ester, the water content in the esterification and the concentration of low-boiling constituents in the crude methacrylic ester can rise continuously overall. In order to avoid this, it may be advantageous to discharge a portion of the water supplied to the system, preferably continuously, from the system. This discharge can in principle be effected, for example, in an order of magnitude in which water is supplied to the system in the prepurification. The aqueous phase removed in the phase separator typically has a content of organic constituents. It may therefore be advantageous to supply this water to a form of disposal which exploits this content of organic substances.

For example, it may be advantageous for water contaminated with organic substances in such a way to be supplied to the combustion space in a sulphuric acid dissociation process. Due to the oxidizable constituents, the calorific value thereof can at least in some cases be utilized. Furthermore, possibly expensive disposal of the water contaminated with organic substances is often thus avoided.

Main Purification of the Methacrylic Ester

For main purification of the methacrylic ester, the crude prepurified methacrylic ester is subjected to another distillation. This involves freeing the crude methacrylic ester of its high-boiling constituents with the aid of a distillation column to obtain a pure methacrylic ester. For this purpose, the crude methacrylic ester is introduced in a manner known to those skilled in the art into the lower half of a distillation column.

The distillation column may in principle correspond to any embodiment which appears suitable to the person skilled in the art. However, it has been found to be advantageous in many cases for the purity of the product obtained when the distillation column is operated with one or more structured packings which meets the following requirements:

Firstly, a minimum level of what are called "dead spaces" should form in the columns, just like in the other pipes through which methacrylic ester flows. The dead spaces lead to a comparatively long residence time of the methacrylic esters, which promote the polymerization thereof. This in turn leads to costly production shutdowns and cleaning of the corresponding parts blocked with polymer. One way of countering the formation of dead spaces is, both through design and through a suitable mode of operation of the columns, to constantly load them with a sufficient amount of liquid that constant flushing of the columns and particularly of the column internals such as structured packings is achieved.

In the purification of the methacrylic ester, the high-boiling constituents thereof are separated from the product by distillation. For this purpose, the column bottom is heated with steam. The bottom temperature is preferably 50 to 80° C., especially 60 to 75° C., at a wall temperature of less than 120° C.

The material obtained in the column bottom is preferably removed continuously and cooled by means of a heat exchanger or a cascade of several heat exchangers to a temperature in a range from 40 to 80° C., preferably 40 to 60° C. and more preferably within a range from 50 to 60° C.

This material, which comprises predominantly methacrylic ester, hydroxyisobutyric ester, methacrylic acid and stabilizer components, is subsequently, via a storage vessel, for example, disposed of or sent to another use. It has been found to be advantageous in many cases for the material obtained in the column bottom to be recycled into the esterification reaction. For example, the material from the column bottom is recycled into the first esterification tank. This gives rise to the advantage that, with regard to a mode of operation of maximum economic viability and a maximum yield, relatively high-boiling compounds present in the column bottom are recycled into the esterification reaction.

At the top of the column, the methacrylic ester purified by distillation is withdrawn and cooled by means of a heat exchanger or a cascade of two or more heat exchangers. The heat from the vapours can be removed by water-cooled heat exchangers or by brine-cooled heat exchangers or by a combination of the two. It has been found to be useful in some cases when the vapours from the distillation column are transferred into two or more heat exchangers connected in parallel, which are operated by means of water cooling. The uncondensed components from the water-cooled heat exchangers can be introduced, for example, into a brine-cooled heat exchanger or a cascade of two or more brine-cooled heat exchangers, which may be arranged in series or in parallel. The condensates obtainable from the heat exchangers are introduced into a collecting vessel and are supplied to a buffer vessel by means of a pump via a further heat exchanger or a cascade of two or more further heat exchangers. The condensate stream is cooled, for example by means of a cascade of one or two water-cooled heat exchangers and one or two brine-cooled heat exchangers, down to a temperature in a range from 0 to 20° C., preferably 0 to 15° C. and more preferably in a range from 2 to 10° C.

A substream is withdrawn from the condensate stream and is recycled via the top of the column into the distillation column. The condensate stream can in principle be fed into the top of the column in any desired manner, for example via distributors. It may, however, be advantageous when a portion of the condensate stream is fed, for example sprayed, into the vapour line above the top of the column. It is also preferable that this feed introduces stabilizer into the top of the column.

A further substream of the condensate intended for recycling into the column can, for example, be branched off before introduction into the vapour line and introduced directly into the top of the column. Here too, it is preferable that this feed introduces stabilizer into the top of the column. The introduction into the top of the column can be accomplished, for example, in such a way that the interior of the top of the column is sprayed with the condensate such that there can be no formation of calm zones in the top of the column, at which the methacrylic ester can polymerize. It may additionally be advantageous when a stabilizer is added for prevention of polymerization to a condensate substream which is recycled into the column. This can be accomplished, for example, by adding an appropriate amount of polymerization inhibitor as a stabilizer to the condensate substream intended for spraying of the top of the column. In some cases it has been found to be advantageous when the condensate substream, downstream of the addition of the stabilizer, but upstream of the entry into the top of the column, passes through a suitable mixing apparatus, preferably a static mixer, in order to achieve very substantially uniform distribution of the stabilizer in the condensate substream.

The uncondensable gaseous substances obtained in the purification process are, for example, sent to disposal.

The crude product present in the buffer vessel is kept, with the aid of a brine cooler, at a temperature of 0 to 20° C., preferably 0 to 15° C., and more preferably within a range from 2 to 10° C.

In order to remove any further impurities from the product and to arrive at ultrapure methacrylic esters, the product can also be subjected to an adsorptive purification stage. It has been found to be useful, for example, when the pure product as a whole, or at least a portion of the pure product, is purified further with the aid of a molecular sieve. Particularly acidic impurities, especially formic acid formed in the preparation process, can thus be removed from the product stream in a simple manner. It has additionally been found to be useful in some cases when the product stream, after passing through the adsorptive purification stage, also passes through one or more filters in order to remove any solids present in the product.

The streams obtained in the workup comprise predominantly polymerizable compounds. In order to prevent the formation of calm zones, it has also been found to be advantageous, in the case of the process described here, when there is a constant flow of methacrylic ester through the parts of the plant which come into contact with methacrylic ester. In a further embodiment of the process presented here, a substream of methacrylic ester is therefore withdrawn downstream of the buffer vessel but upstream of the adsorptive purification stage, in order to flush the top regions of those heat exchangers which accommodate the vapours originating from the distillation column.

Overall, it has been found to be advantageous in the context of the present invention when the integrated system composed of prepurification and main purification is configured such that the prepurification removes substances having a lower boiling point than the methacrylic ester and these substances are subsequently condensed by cooling, leaving uncondensed residual substances in the gas phase, the main purification removes substances which have a higher boiling point than the methacrylic ester and the latter is condensed by cooling, leaving uncondensed residual substances in the gas phase, and uncondensed gaseous residual substances from the prepurification and uncondensed gaseous residual substances from the main purification are subjected to a common postcondensation.

A condensate obtained in such a common postcondensation can advantageously be subjected to a phase separation, which can form an aqueous phase and an organic phase.

In this case, for example, the aqueous phase can be recycled fully or partly into the esterification, or the organic phase can be recycled fully or partly into the prepurification, or both.

The product obtained overall in the purification stage is subsequently withdrawn from the purification stage with a temperature in a range from −5 to 20° C., preferably 0 to 15° C. and more preferably within a range from 2 to 10° C.

Description of the Drawing (FIG. 1)

Step d) Hydrolysis of the Methacrylic Esters to Methacrylic Acid

The methyl methacrylate (1) synthesized via the precursors, or the respective methacrylic ester, and the water (2) required for hydrolysis to methacrylic acid, are supplied to the plant.

After the introduction, the reactants are combined with the circulation streams (3) and (4). The mixture is supplied to a heat exchanger (5), by which the reaction mixture is brought to the desired reaction temperature. Subsequently, the reaction mixture is supplied to a fixed bed tubular reactor (6). The fixed bed tubular reactor preferably contains heterogeneous catalysts. The catalysts are selected from the group of the zeolites, ion exchange resins or amorphous acid catalysts. Particular preference is given to cationic ion exchange resins, especially the ion exchanger of the Lewatit K2431 type from Lanxess AG.

Depending on the polymerization tendency of the monomer mixture used, the type of catalyst and/or the size of the catalyst bed, the flow through the catalyst bed is from the top or from the bottom. Preference is given to inflow from the bottom, and to supply of the reaction mixture via the catalyst bed base.

Over this catalyst, the hydrolysis of methyl methacrylate or of the respective methacrylate takes place to give methacrylic acid. There follows, by way of example, a description of the hydrolysis of methyl methacrylate to methacrylic acid. Corresponding adaptations for other methacrylic esters can be conducted in the manner known to the person skilled in the art.

It has been found that a low $H_2O$ concentration in the reaction stream of <10% by weight, preferably <5% by weight, and especially <1% by weight leads to a distinct rise in the steam required to remove the methanol/methyl methacrylate azeotrope.

Since, however, the conversion and the space-time yield fall when the $H_2O$ concentration is reduced, the optimum $H_2O$ concentration has to be established.

In order to ensure the presence of a homogeneous liquid reaction phase even at reaction temperatures above the boiling point of the mixture, the reactor can be operated under a slightly elevated pressure of approx. 2 to 4 bar.

The methanol formed in the reaction is removed as an azeotrope with methyl methacrylate as the top stream (8) in a downstream rectifying column (7). The majority of the bottom stream can be recycled as circulation stream (4). A portion will be conducted into a vacuum rectifying column (10) for low boiler removal via a flash chamber (9). Methyl methacrylate and $H_2O$, and also residual methanol, are removed (3) therein via the top of the column, and can be recycled again.

The methacrylic acid enriched in the bottom of the column can be removed (11) in the form of crude methacrylic acid. The methacrylic acid is preferably separated in a further downstream vacuum rectifying column (12) from the high boilers present (14) (stabilizers, by-products) and obtained in the form of pure methacrylic acid (13) via the top of the column. The methacrylic acid thus obtained has a purity of >99.5%.

For further optimization of the overall process, the methanol/methyl methacrylate mixture (8) can be recycled into process step c). Typically the mixture of methanol with methyl methacrylate has a near-azeotropic composition described in the literature, in operating practice a composition of at least 60% methanol, preferably at least 75% methanol. The methanol present in the mixture can be reused for esterification of methacrylamide.

LIST OF REFERENCE SYMBOLS

1 Methyl methacrylate (MMA) feed
2 Water feed
3 Circulation stream from rectifying column for methanol removal
4 Circulation stream from vacuum rectifying column for low boiler removal
5 Heat exchanger
6 Reactor
7 Rectifying column for methanol removal
8 Top stream of the rectifying column for methanol removal
9 Flash chamber
10 Vacuum rectifying column for low boiler removal
11 Bottom stream of the vacuum-rectifying column for low boiler removal
12 Vacuum rectifying column for methacrylic acid removal
13 Methacrylic acid stream
14 High boiler stream The examples given hereinafter are given for better illustration of the present invention, but are not intended to restrict the invention to the features disclosed herein.

EXAMPLES

Example 1

Acetone cyanohydrin is obtained (a) from the base-catalysed reaction of hydrogen cyanide with acetone. The hydrolysis to methacrylamide (b) is followed by transesterification (c) in the presence of methanol to give methyl methacrylate.

12.7 kg/h of methyl methacrylate (1) are combined with 2.1 kg/h of water (2). The reaction mixture is brought, together with 15.4 kg/h of circulation stream (3) with 500 kg/h of circulation stream (4), to a temperature of 110° C. by means of a heat exchanger (5), and conducted from below through the reactor (6) filled with the cationic ion exchange resin Lewatit K2431 from Lanxess AG. Over this cationic ion exchange resin, the hydrolysis of methyl methacrylate to methacrylic acid takes place. The conversion is effected at a pressure of 3 bar gauge, measured at the reactor outlet.

The methanol formed in the reaction is removed (8) as a top stream at 4.8 kg/h in a downstream rectifying column (7) as an azeotrope with methyl methacrylate, and is returned to the methyl methacrylate preparation (c). From the bottom of the rectifying column (7), 500 kg/h of circulation stream (3) are recycled; the remaining 25.4 kg/h are conducted from the bottom of the column to the low boiler removal by means of a flash chamber (9) into a further vacuum rectifying column (10). The low boilers present, methyl methacrylate, water and residual methanol, are distilled therein via the top of the column and returned as a circulation stream at 15.4 kg/h (3). The methacrylic acid stream of 10.0 kg/h (11) enriched in the bottom of the column is purified in a further downstream vacuum rectifying column (12) and removed (13) via the top. High boilers are discharged (14) via the bottom.

Example 2

The sulphuric acid required for the conventional methacrylic acid production was determined in a methyl methacrylate/methacrylic acid integrated system. For this purpose, the sulphuric acid required for the process according to the invention for preparation of methacrylic acid was determined.

The conventional methacrylic acid was prepared via the hydrolysis of the amide.

|  | Conventional methacrylic acid preparation | Inventive methacrylic acid preparation | Difference |
|---|---|---|---|
| $H_2SO_4$ consumed | 178 kt | 174 kt | 4 kt |
| Waste acid obtained | 255 kt | 247 kt | 8 kt |
| Water content in waste acid | 27% | 17.5% | 9.5% |
| Water content in MA | 1500-2000 ppm | <1000 ppm | 500-1000 ppm |

The process according to the invention saves large amounts of sulphuric acid. In addition, the amount of waste acid can be greatly reduced.

The waste acid consists for the most part of sulphuric acid and ammonium sulphate. This mixture is fed into a sulphuric acid dissociation plant.

The invention claimed is:

1. A process for preparing methacrylic acid, the process comprising:
   converting acetone cyanohydrin to methacrylamide;
   esterifying the methacrylamide in the presence of at least one alcohol, thereby obtaining at least one methacrylic ester; and
   hydrolyzing the at least one methacrylic ester in the presence of at least one heterogeneous catalyst, thereby obtaining methacrylic acid,
   wherein:
   a feed stream to the hydrolyzing comprises a water stream, and a methacrylic ester stream from the esterifying;
   a recirculation stream to the hydrolyzing comprises a first circulation stream from the input of a vacuum rectifying column for low boiler removal, and a second circulation stream from the output of a rectifying column for alcohol removal; and
   the mass ratio or the volume ratio of the recirculation stream to the feed stream ranges from 5-50.

2. The process according to claim 1, wherein the at least one heterogeneous catalyst is selected from the group consisting of a zeolite, an ion exchange resin, and an amorphous acid catalyst.

3. The process according to claim 1, wherein, during the hydrolyzing, the flow through a catalyst bed is from bottom or from top.

4. The process according to claim 1, wherein the hydrolyzing occurs at a temperature of 50-200° C.

5. The process according to claim 1, wherein the hydrolyzing occurs at an elevated pressure.

6. The process according to claim 1, wherein the ratio of the at least one methacrylic ester to water in the hydrolyzing is between 0.5 and 5.

7. The process according to claim 1, wherein the residence time during the hydrolyzing is 10-120 min.

8. The process according to claim 1, wherein the mass ratio or the volume ratio of the recirculation stream to the feed stream ranges from 15 to 30.

9. The process according to claim 1, wherein a methanol/methyl methacrylate mixture is supplied during said esterifying.

10. The process according to claim 1, wherein the hydrolyzing occurs at a temperature of 70-150° C.

11. The process according to claim 1, wherein the hydrolyzing occurs at a temperature of 90-120° C.

12. The process according to claim 1, wherein the hydrolyzing occurs at a temperature of 100-110° C.

13. The process according to claim 1, wherein the hydrolyzing occurs at an elevated pressure of from 0.1 to 9 bar gauge.

14. The process according to claim 1, wherein the hydrolyzing occurs at an elevated pressure of from 2 to 4 bar gauge.

15. The process according to claim 1, wherein the ratio of the at least one methacrylic ester to water in the hydrolyzing is between 1 and 4.

16. The process according to claim 1, wherein the ratio of the at least one methacrylic ester to water in the hydrolyzing is between 1.5 and 3.

* * * * *